United States Patent [19]

Preston

[11] Patent Number: 4,654,207
[45] Date of Patent: Mar. 31, 1987

[54] PEARLESCENT SHAMPOO AND METHOD FOR PREPARATION OF SAME

[75] Inventor: John C. Preston, Chicago, Ill.

[73] Assignee: Helene Curtis Industries, Inc., Chicago, Ill.

[21] Appl. No.: 711,234

[22] Filed: Mar. 13, 1985

[51] Int. Cl.$^4$ .......................... A61K 7/06; A61K 7/09; A61K 7/11

[52] U.S. Cl. ............................ 424/70; 252/DIG. 13; 424/71; 424/72; 514/844

[58] Field of Search .......................................... 424/70

[56] References Cited

U.S. PATENT DOCUMENTS

| 4,102,795 | 7/1978 | Minegishi et al. | 424/70 |
| 4,126,674 | 11/1978 | Mausner | 424/70 |
| 4,384,974 | 5/1983 | Guthauser | 424/170 |
| 4,438,096 | 3/1984 | Preston | 424/70 |
| 4,503,033 | 3/1985 | Bouillon et al. | 549/445 |

FOREIGN PATENT DOCUMENTS 56-71021  6/1981  Japan ........................ 424/70

Primary Examiner—Dale R. Ore
Attorney, Agent, or Firm—Dressler, Goldsmith, Shore, Sutker, & Milnamow, Ltd.

[57] ABSTRACT

The present invention relates to improved pearlescent shampoos having suspended therein in a crystalline state a pearlescing agent comprised of a fatty acid ester whose fatty acid portion is derived from a saturated ($C_{16}$–$C_{22}$) fatty acid and whose alcohol portion is derived from a saturated ($C_{14}$–$C_{22}$) fatty alcohol, the ester being presolubilized with a substantially anhydrous solubilizing agent by a method of this invention.

26 Claims, No Drawings

PEARLESCENT SHAMPOO AND METHOD FOR PREPARATION OF SAME

TECHNICAL FIELD

The present invention relates to shampoo compositions, and particularly to a pearlescent shampoo and a method of preparing a pearlescent shampoo that contains a suspended pearlescing agent comprised of a fatty acid ester presolubilized with a substantially anhydrous solubilizing agent.

BACKGROUND ART

Liquid creme or lotion shampoo formulations are often opacified by deliberately incorporating "pearlescing" agents therein to achieve a cosmetically attractive pearl-like appearance known as pearlescence.

Not all useful opacifiers, however, are pearlescing agents. Several materials are known to be useful for creating pearlescence in cosmetic compositions, simulated pearls and lacquers. These materials are sometimes lustrous, silvery-white substances derived from naturally occurring and inorganic materials, such as comminuted fish scales, natural mineral mica, mercuric chloride and shellfish nacres, or are synthetic forms of mother-of-pearl.

Pearlescing agents frequently utilized in cosmetic compositions may be stearic acid and insoluble metal salts thereof, such as magnesium stearate or zinc stearate, glyceryl stearates, ethylene glycol mono- and distearates, polyethylene glycol distearate, glycol amidostearate, less soluble surfactants having a high cloud point, such as ($C_{16}$–$C_{18}$) alkyl glyceryl ether sulfonates, certain fatty alkanolamides, and even insoluble resin latex dispersions.

The type of pearlescence achieved may vary from flat to highly reflective or iridescent depending on the amount, size, shape and reflective or refractive power of the pearlescing agent used as the opacifier.

The known pearlescent materials suffer from several disadvantages. For example, non-separating, stable pearlescent compositions that contain a relatively large amount of water, such as shampoos, have been difficult to prepare. That is, once prepared, such compositions tend to separate during storage into two distinct phases, one of which contains a large amount of the pearlescent material.

Persons skilled in the art are aware of the problems faced by shampoo manufacturers in consistently preparing a pearly or pearlescent shampoo. A detailed discussion of these problems is found in the article "Opacifiers and pearling agents in shampoos" by Hunting, *Cosmetics & Toiletries*, Vol. 96, (hereinafter "Hunting") 65–78 (July, 1981), incorporated herein by reference. A particular problem, as described by Hunting, is the influence of the method or procedure used in preparing the shampoo, as well as the order in which the ingredients are incorporated.

Cosmetic compositions that contain ethylene glycol monostearate or distearate as a pearlescing agent can be made relatively stable to phase separation at ambient room temperatures. However, when the temperature of the composition is elevated near, to, or above the melting point of the pearlescer during summer storage or in a window display of a product, the composition must be cooled with agitation to return it to a pearlescent condition.

Another disadvantage of these compositions is that a generous amount of suspended pearl producing opacifier is required to produce pearlescence. Ethylene glycol monostearate or distearate, for example, are each typically utilized in amounts of about 1.5 to about 3.5 weight percent of the shampoo composition. When so used, those pearlescers also tend to interfere with lathering.

A disadvantage of some of the known particulate pearlescent materials such as comminuted fish scales, mica or shellfish nacre is that these pearlescers can be abrasive when used in a shampoo that is intended to be rubbed on the scalp and hair.

On the other hand, non-particulate, non-abrasive, wax-like pearlescers depend on their being suspended in the liquid medium in a crystalline state to produce pearlescence. These pearlescers, however, have several disadvantages. The compositions must frequently be stored and aged over a period of several weeks or more before the pearlescer reaches a satisfactory crystalline state. Such aging storage is commercially impractical, since the quality and consistency of the result is not readily predictable. Additionally, the viscosity of shampoos prepared with such pearlescers tends to continuously change to some unpredictable level after pearlescence initially develops, thereby presenting added product quality control problems.

In my U.S. Pat. No. 4,438,096, issued Mar. 20, 1984, to the assignee of this invention, I teach the use of the fatty acid ester, myristyl myristate, as the pearlescing agent for a shampoo prepared by a direct-type method disclosed therein. The teachings of that patent are incorporated herein by reference, and the method of preparing a shampoo of that patent is also referrred to as the "Preston" method.

In the Preston method, the myristyl myristate was admixed directly with the liquid medium of the composition, while the ester was in a liquid state and the liquid medium was heated to a temperature above the melting point of myristyl myristate. The liquid medium contained water and an amount of surface active agent effective for cleansing.

Myristyl myristate was noted in my above patent as being a singularly useful pearlescing agent in the group of fatty alcohol esters of fatty acids that are homologous esters of myristyl myristate for shampoos prepared according to the method taught therein. For example, cetyl palmitate did not form a pearlescent shampoo when it was substituted for myristyl myristate.

My patent also teaches that at low levels of about 0.2 weight percent of myristyl myristate, pearlescence developed slowly over an aging period of about two weeks, and that in amounts greater than about 1 weight percent of the shampoo, phase separation of the fatty acid ester from the rest of the shampoo took place. Thus, where the total amount of pearlescing agent used fell outside the range of about 0.25 to about 1 weight percent of the total composition, the addition of phase-stabilizing ingredients was needed for preparation of stable, non-separating pearlescent compositions.

There is a need, therefore, for a pearlescing agent and method of preparing a pearlescent product capable of producing a consistently predictable pearlescence, especially in a shampoo, within a commercially reasonable time period.

SUMMARY OF THE INVENTION

The present invention relates to an improved pearlescent shampoo and method for preparation of same that contains a novel non-particulate, presolubilized pearlescing agent suspended therein in a crystalline state. More particularly, the pearlescing agent is a non-liquid presolubilized natural or synthetic fatty acid ester, the ester being presolubilized in the manner disclosed herein with a substantially anhydrous solubilizing agent.

Pearlescent shampoo compositions of this invention having a predictable pearlescence are consistently obtained when the ratio of solubilizing agent to ester is in the range of from between about 1 to about 25 parts by weight of solubilizing agent per part of ester, and the shampoo is prepared by an Indirect method disclosed herein.

An improved pearlescent shampoo of this invention comprises a liquid medium containing an effective amount of a cleansing surface active agent and water, and having admixed therein an effective amount of a substantially anhydrous pearlescing base comprising a presolubilized pearlescing agent and anhydrous solubilizing agent for the pearlescing agent as disclosed herein. The term "substantially anhydrous" as used herein refers to a material or a composition that does not contain more than 10 percent water, i.e., the material or composition is from about 90–100 percent active.

In one embodiment, the substantially anhydrous pearlescing base comprises, as a presolubilized pearlescing agent, at least one fatty acid ester whose fatty acid portion is derived from a saturated ($C_{16}$–$C_{22}$) fatty acid and whose alcohol portion is derived from a saturated ($C_{14}$–$C_{22}$) fatty alcohol, and the pearlescing agent is presolubilized by the method of this invention with a substantially anhydrous solubilizing agent at a weight ratio of from about 1 to about 25 parts by weight of solubilizing agent per part of ester.

The method of this invention is identified herein as an "Indirect" method, since the pearlescing agent is presolubilized and contained in a substantially anhydrous pearlescing base prepared separately from the main body or liquid medium of the shampoo. Thus, the pearlescing agent is not added directly to the shampoo in the manner taught by me in my patent, or in the manner customarily practiced.

In the Indirect method of this invention, a pearlescing base is prepared by blending a substantially anhydrous solubilizing agent for the fatty acid ester at a temperature, prior to the blending step, above the melting point of the fatty acid ester pearlescing agent and below the boiling point of the solubilizing agent. While the temperature range is so maintained and the solubilizing agent is in a liquid state, the pearlescing agent is solubilized therein to form a pearlescing base.

The liquid medium of the composition is heated to and maintained at a temperature above that of the melting point of the fatty acid ester present in the pearlescing base and below the boiling point of the liquid medium. The heated pearlescing base and heated liquid medium are thereafter admixed while the pearlescing base in a liquid state. The temperature of the admixture is thereafter reduced to a temperature range below the melting point of the pearlescing agent to form a substantially pearlescent shampoo having the pearlescing agent suspended therein in a crystalline state.

In a preferred embodiment, an improved pearlescent shampoo prepared by the method of this invention comprises, per 100 parts by weight thereof, water having dispersed therein about 5 to about 20 parts by weight of a cleansing surface active agent, about 0.20 to about 5 parts by weight pearlescing base comprised of a fatty acid ester pearlescing agent, the ester being presolubilized in the manner disclosed herein with a substantially anhydrous solubilizing agent at a weight ratio of from about 4 to 15 parts of solubilizing agent per part of ester. The pearlescent shampoo does not separate into a distinct phase during storage at ambient room temperature.

The present invention has several benefits and advantages. One benefit is that pearlescent shampoos prepared in the manner disclosed herein remain in a pearlescent condition at higher temperatures, such as those encountered during summer storage conditions or in a store window display, than do pearlescent shampoos prepared in a conventional manner. Further, these shampoos return to a pearlescent condition at ambient room temperature after being heated to a temperature above the melting point of the fatty acid ester pearlescing agent without the need of cooling with agitation.

A further benefit of this invention is that the pearlescing agent does not substantially interfere with the lathering of the shampoo as do ethylene glycol mono- and di-stearates when each material is present in an amount sufficient to pearlesce.

A still further benefit is that a shampoo prepared by the method of this invention develops an elegant pearlescence within a practical crystallization period of within 5 days' aging at a temperature below the melting point of the fatty acid ester pearlescing agent. Additionally, the pearly effect is of iridescent-like quality on swirling, shaking, stirring, or otherwise similarly disturbing the shampoo without using the particulate pearlescers normally required for this effect.

An even further benefit is that a pearlescent shampoo of this invention has a viscosity that remains substantially unchanged once pearlescence has developed.

A shampoo prepared according to the Indirect method of this invention has an added advantage in that the time for pearlescence to develop can be accelerated. This is accomplished by dispersing a low level of a pearlescence accelerating agent into the shampoo composition immediately prior to reducing the temperature of the shampoo below the melting point of the pearlescing agent.

Yet another benefit of the present invention is that the pearlescing agent is not abrasive to the hair or scalp during the shampooing process unlike comminuted, particulate pearlescers.

Still further benefits and advantage of the present invention will be apparent to those skilled in the art from the detailed description of the invention, examples and claims that follow.

DETAILED DESCRIPTION OF THE INVENTION

The present invention relates to aqueous shampoo compositions that are pearlescent. Pearlescence in these compositions is achieved through a novel presolubilized pearlescing agent; i.e., a fatty acid ester whose fatty acid portion is derived from a saturated ($C_{16}$–$C_{22}$) fatty acid and whose alcohol portion is derived from a saturated ($C_{14}$–$C_{22}$) fatty alcohol, preferably a saturated ($C_{14}$–$C_{18}$) fatty alcohol. The pearlescing agent is presolubilized with a substantially anhydrous solubilizing agent as defined hereinbefore in the manner described herein.

It has now been surprisingly found that substantially stable, non-separating pearlescent shampoo compositions, free of the phase-stabilizing ingredients utilized in my previous patent, can be prepared that contain a greater amount of fatty acid ester; i.e., in a range of about about 1 to about 2.5 weight percent per 100 parts of shampoo in the Indirect method of this invention. Further, a pearlescent shampoo of this invention contains a pearlescing agent that is any one member of the group of fatty alcohol esters of fatty acids that are longer chain homologous esters of myristyl myristate presolubilized in the manner disclosed herein. It has further been found that pearlescence can be achieved within a commercially practical aging period of less than a week's time with low levels of at least one of these fatty acid esters; i.e., amounts falling in a range of about 0.01 to 0.2 parts by weight per 100 parts of shampoo composition.

On the other hand, when myristyl myristate was used as the sole fatty acid ester pearlescing agent present in the pearlescing base, pearlescence developed slowly over a period of several weeks, even when the amount of myristyl myristate in the shampoo was increased to a range of between about 0.25 to about 1 parts by weight per 100 parts of shampoo, i.e.: the preferred range under the "Preston" method. However, myristyl myristate may be included at a low level in admixture with its homologues without delaying pearlescence formation in a shampoo of this invention.

The fatty acid ester pearlescing agent is presolubilized with a substantially anhydrous solubilizing agent by blending the solubilizing agent and ester at a ratio of about 1 to about 25 parts by weight of solubilizing agent per part of ester, preferably about 4 to about 15 parts by weight. Prior to said blending, the solubilizing agent is in a liquid state and is at a temperature above the melting point of the fatty acid ester and below the boiling point of the solubilizing agent. The blend is maintained within this temperature range until the ester is solubilized. This solubilization process provides a substantially anhydrous pearlescing base. It is to be understood that any reference hereinafter to "pearlescing base" or "solubilizing agent" refers to a substantially anhydrous pearlescing base or substantially anhydrous solubilizing agent.

More particularly, the present invention further relates to a method of suspending the pearlescing agent in a crystalline state in a shampoo as disclosed herein using a pearlescing base.

The method of this invention is referred to herein as an "Indirect" method, since a substantially anhydrous pearlescing base, containing a presolubilized pearlescing agent and its solubilizing agent is prepared separately from the main body of the shampoo. The pearlescing base, so prepared, is subsequently admixed with the main body of the shampoo under the temperature and conditions described in detail hereinbelow in the Methods Section A.

The upper limit of the temperature used for preparing a pearlescent shampoo by the Indirect method has not been fully explored. However, as a matter of common expediency, a temperature above the melting point of the fatty acid ester pearlescing agent and below the boiling point of the solubilizing agent is used for preparing the pearlescing base. Likewise, the liquid medium is heated to a temperature above the melting point of the fatty acid ester present in the pearlescing base and below the boiling point of the liquid medium, prior to admixing the pearlescing base therein, while the pearlescing base is still in a liquid state.

Those skilled in the art will recognize that the upper limit of the temperature to which the liquid medium is heated is preferably below the boiling point of water or of the lowest boiling ingredient in the shampoo composition present at the time the liquid medium and the pearlescing base are admixed. In actual practice a useful temperature is in the range of about 40° C. to about 85° C. (about 104° F. to about 185° F.), preferably in the range of about 40° C. to about 60° C. (about 140° F.), for preparing a shampoo of this invention.

A conventional method of preparing a pearlescent shampoo, i.e., by adding an unsolubilized pearlescing agent directly to the main body of the shampoo, is referred to herein as a "Direct" method. This method is also described in detail hereinbelow in Section A.

It is to be understood that the term "main body" of the shampoo means the "liquid medium" portion that comprises water having dispersed therein cleansing surface-active agents and optional shampoo components other than the pearlescing agent, as described herein.

The amount of pearlescing base present per 100 parts of shampoo may be from between about 0.1 to about 20 parts by weight, preferably from between about 0.1 to about 10, more preferably from between about 0.5 to about 5 parts by weight. So long as the ratio of fatty acid ester to solubilizing agent comprising the pearlescing base falls within the range of this invention, the upper limit on the amount of pearlescing base used is more a matter of convenience and economy.

It is to be understood that the term "fatty acid ester" is used herein to refer to useful fatty alcohol esters of fatty acids whose fatty acid portion is derived from a saturated ($C_{16}$–$C_{22}$) fatty acid and whose alcohol portion is derived from a saturated ($C_{14}$–$C_{22}$) fatty alcohol. The fatty acid esters useful herein are thus, longer chain higher melting homologues of myristyl myristate. The fatty acid esters may be derived from natural or synthetic materials, and are crystalline solids preferably having a melting point above about 35° C. (above 95° F.), more preferably above 40° C. (above 104° F.).

The word "fatty" is used herein to refer to carbon atom chains that contain about 8 to about 22 carbon atoms. More specifically, the word "fatty" is used in conjunction with pearlescing esters whose carboxylic acid chains are derived from acids containing 16–22 carbon atoms, and whose alcohol chains contain 14–22 carbon atoms. The word "fatty" is also utilized for surfactants, solubilizing agents and other ingredients that may contain chains of about 8 to about 22 carbon atoms.

The fatty acid ester content per 100 parts of pearlescing base may be in an amount corresponding to about 0.01 to about 2.5 parts by weight of the finished shampoo composition, preferably in an amount of about 0.01 to about 1.0 parts by weight, more preferably at an amount of about 0.05 to about 0.8 parts by weight.

The lower limit of fatty acid ester appears to be of import to the novel pearlescing of the shampoo of this invention, while the upper limit relates more to convenience. Quantities of fatty acid ester greater than 2.5 parts by weight per 100 parts of shampoo composition may be used in preparing a pearlescing base of this invention, but it is wasteful to use such quantities.

Exemplary useful fatty acid esters include, but are not limited to, myristyl palmitate, myristyl stearate, cetyl myristate, cetyl palmitate, cetyl stearate, stearyl myristate, stearyl palmitate, stearyl stearate, stearyl behenate, and mixtures thereof. Particularly preferred esters are myristyl stearate, stearate stearate, stearyl myristate, cetyl palmitate and stearyl palmitate. A small amount of myristyl myristate may be included in a pearlescing base containing one or more of the foregoing fatty acid esters, if desired.

The solubilizing agent for the fatty acid ester may itself be a cosmetically useful material but its cosmetic functionality is not essential to the invention. For example, the substantially anhydrous solubilizing agent may aid in boosting the foam produced by the shampoo or may be an auxiliary cleansing surface active agent or an auxiliary cosmetic adjuvant for conditioning the hair.

The total amount of solubilizing agent present per 100 parts of shampoo may be from about 0.01 to about 15 parts by weight, preferably from about 1.0 to about 10, more preferably from about 2.5 to about 5 parts by weight. Persons skilled in the art will appreciate that the upper limit of the amount of the solubilizing agent used is a matter of convenience and economic prudence, so long as the ratio of fatty acid ester to solubilizing agent falls within the teachings of this invention.

Exemplary solubilizing agents that are substantially anhydrous include, but are not limited to, natural or synthetic linear or branched chain polyoxy($C_2$–$C_4$)alkylene derivates of ($C_8$–$C_{22}$) fatty alcohols containing from about 1 to about 50 oxyethylene units per molecule, or oxypropylene units per molecule, or oxyethylene/oxypropylene condensation units per molecule, preferably from about 1 to about 25 units, more preferably from about 1 to about 10 oxyethylene, or oxypropylene, or oxyethylene/oxypropylene units per molecule, polyoxyethylene derivatives of ($C_8$–$C_{22}$) alkyl phenols containing an average of from about 3 to about 150 oxyethylene units per molecule, preferably from about 3 to about 100, more preferably from about 3 to about 40 oxyethylene units per molecule, copolymers of ethylene oxide and propylene oxide, mono- and di-($C_2$–$C_4$) alkanolamides of ($C_8$–$C_{22}$) fatty acids, alkali metal salts of fatty ($C_{14}$–$C_{18}$) alkyl sulfates and the like.

The foregoing solubilizing agents are commercially available from a number of well-known suppliers, that are extensively listed in (a) the *CTFA Cosmetic Ingredient Dictionary* (hereinafter *CTFA Dictionary*), Third Edition, published by the Cosmetic, Toiletry and Fragrance Association (1982), and in (b) the 1984 Edition of the *Cosmetic Bench Reference, an encyclopaedia of cosmetic materials* (hereinafter *Bench Reference*), found in the August 1984 edition and its addenda found in the December, 1984 edition of *Cosmetics & Toiletries Magazine*. The disclosures of the *CTFA Dictionary* and *Bench Reference* are incorporated herein by reference.

Illustrative fatty alcohols containing oxyethylene units are the polyethylene glycol ethers of lauryl alcohol given the *CTFA* names of laureth-1 through laureth-10, the polyethylene glycol ethers of stearyl alcohol given the *CTFA* names of steareth-2 through steareth-100, and the polyethylene glycol ethers of a mixture of synthetic ($C_9$–$C_{15}$) fatty alcohols given the *CTFA* names Pareth-15-5, through Pareth-15-12, Pareth-25-3 through Pareth-25-12, Pareth-45-7 through Pareth-45-13, Pareth-91-6 and Pareth-91-8 sold under the trademark Tergitol by Union Carbide Corporation, Danbury, Conn., and under the trademark Neodol by Shell Chemical Company, where the last numeric suffix denotes the average number of oxyethylene units per molecule.

Illustrative fatty alcohols containing oxypropylene units are the polypropylene glycol ethers of cetyl alcohol given the *CTFA* names PPG-10 cetyl ether, PPG-28 cetyl ether and PPG-50 cetyl ether, where the numeric suffix denotes the average number of oxypropylene units per molecule.

Illustrative fatty alcohols containing oxyethylene/oxypropylene units are the polyoxypropylene/polyoxyethylene ethers of cetyl alcohol given the *CTFA* names PPG-4-ceteth-1, PPG-4-ceteth-110, PPG-5-ceteth-20, PPG-8-ceteth-2 and the like, where the first numeric suffix denotes the average number of polyoxypropylene units and the second numeric suffix denotes the average number of polyoxyethylene units per molecule.

Illustrative alkyl phenols containing oxyethylene units are the polyoxyethylene nonyl phenyl ethers given the *CTFA* names nonoxynol-2 through nonoxynol-100, where the numeric suffix denotes the average number of oxyethylene units. Illustrative copolymers of ethylene oxide and propylene oxide are the block polymer series found under the *CTFA* names POLOXAMER 101 through POLOXAMER 407.

Illustrative alkanolamides are the monoethanolamine lauric acid amide given the *CTFA* name Lauramide MEA, the diethanolamine coconut fatty acid condensate given the *CTFA* name, Cocamide DEA and the monoisopropanolamine myristic acid amide given the *CTFA* name Myristamide MIPA.

Illustrative alkali metal salts of fatty alkyl sulfate include sodium lauryl sulfate, sodium myristyl sulfate and sodium tallow sulfate found in the *CTFA Dictionary* under these names.

It is to be understood that the foregoing materials are intended to be illustrative, and are not limiting.

Further substantially anhydrous compounds that may be suitable solubilizing agents also include, but are not limited to, anhydrous cosmetic emollients, such as polyethylene glycols, isopropyl palmitate, isopropyl myristate, mineral oils, silicone oils and the like.

It should be understood that a useful amount of the foregoing materials can be easily determined by a skilled formulator to avoid interfering with the foaming and cleansing action normally expected of a shampoo composition. It should be further understood that a pearlescing base of this invention may contain at least one of the forementioned solubilizing agents or mixtures thereof.

Particularly useful solubilizing agents are also nonionic surface active agents supplied as 100 percent active solids or fluids. As such, they may be selected for their known cosmetic functionality as well. In such instances, the solubilizing agent may also be present among the surface active agents present in the liquid medium of the shampoo.

Among suitable nonionic surface active agents, those that are particularly preferred include, but are not limited to, polyoxyethylene derivatives of ($C_{12}$–$C_{18}$) fatty alcohols containing from about 4 to about 25 oxyethylene units per molecule, such as polyoxyethylene (20) cetyl ether and polyoxyethylene (4) lauryl ether; polyoxyethylene derivatives of octyl- and nonylphenols containing an average of from about 4 to about 30 oxyethylene units, such as polyoxyethylene (9) octylphenyl ether and polyoxyethylene (15) nonylphenyl ether, mono- and di-($C_2$–$C_4$) alkanolamides of fatty acids having from about 12 to 18 carbon atoms such as N-(2-hydroxyethyl) coco fatty acid amide, N,N-bis-(2-hydroxyethyl) coco fatty acid amide, N, N-bis-(2-hydroxyethyl) lauramide, and the like.

When the foregoing nonionic surface active agents are utilized as the substantially anhydrous solubilizing agent of this invention, they are excluded from the calculation of the total amount of cleansing surface active agent present in the liquid medium of the shampoo. Such surface active agents are discussed hereinafter.

The substantially anhydrous solubilizing agents disclosed hereinabove are principally used to solubilize the fatty acid ester pearlescing agent in forming the pearlescing base. However, advantage may also be taken of their foaming, wetting, detergent, dispersing, emulsifying or emollient conditioning properties.

In addition to water, which can be from about 60 to about 90 parts by weight of the shampoo composition, the aqueous liquid medium of the shampoo includes an amount of surface active agent dispersed therein that is effective for cleansing.

A useful amount of total surface active agent effective for cleansing is present in 100 parts of a shampoo of this invention in the range of from between about 5 to about 25 parts by weight of the shampoo, preferably from about 5 to about 20 parts by weight. It is to be understood that the total amount of surface active agent in parts by weight denotes active parts by weight material; the upper limit being selected as a matter of convenience and economy.

The cleansing surface active agents useful in shampoos of this invention can be anionic, cationic, nonionic, zwitterionic or amphoteric. Typically useful surface active agents contain at least one fatty 12 to 22 carbon atom chain. The individual surface active agents can also be used in mixtures of two or more surface active agents or their salts.

The phrase "cleansing surface active agents" refers herein to those surface-active agents whose primary cosmetic function in the shampoo is a detersive one of removing soil from the hair.

Exemplary anionic surface active agents include but are not limited to the alkali metal, a primary, secondary or tertiary ($C_2$–$C_4$) alkanolamine or ammonium salts of the following: a fatty ($C_8$–$C_{18}$) alkyl sulfate, a fatty ($C_8$–$C_{18}$) alkyl polyoxyethylene sulfate having from about 1 to about 4 oxyethylene units, an alkyl ($C_{12}$–$C_{18}$) sarcosinate, an alkyl ($C_{12}$–$C_{18}$) isethionate, an alkyl ($C_{12}$–$C_{18}$) taurate, a mono- or di-alkyl($C_8$–$C_{12}$)sulfosuccinate, a fatty ($C_{12}$–$C_{16}$) alpha-olefin sulfonate and mixtures thereof.

Among the anionic surface active agents that are useful, those that are particularly preferred are ammonium lauryl sulfate, sodium lauryl sulfate, ammonium lauryl polyoxyethylene sulfate having an average of 1–4 oxyethylene units per molecule, sodium lauryl polyoxyethylene sulfate having an average of 1–4 oxyethylene units per molecule, triethanolamine lauryl sulfate, triethanolamine lauryl polyoxyethylene sulfate having an average of 1–4 oxyethylene units per molecule, sodium lauroylsarcosinate, sodium lauroyl isethionate, sodium methyl cocoyltaurate, sodium cetylstearyl sulfate, disodium lauryl sulfosuccinate, sodium di-(2-ethylhexyl) sulfosuccinate; and a sodium alpha-olefin sulfonate prepared from mixed olefins having about 12 to 18 carbon atoms in the fatty chain, and mixtures thereof.

Additional suitable anionic surface active agents include the alkali metal, primary, secondary and tertiary alkanolamine, and ammonium soaps of natural or synthetic linear and branched chain fatty acids having 12 to 22 carbon atoms in the fatty chain. Exemplary fatty acids include lauric, myristic, palmitic, stearic, oleic, ricinoleic, capric, arachic, behenic, and isostearic acids, coconut fatty acids, hydrogenated coconut fatty acid and tallow acids. Illustrative soaps are potassium oleate, sodium laurate, ammonium stearate, monoethanolamine palmitate, diethanolamine oleate, and triethanolamine isostearate.

Anionic surface active agents may be present in an amount of about 5 to about 25 parts by weight, preferably in an amount of about 5 to about 20 parts by weight per 100 parts of the shampoo.

Exemplary cationic surface active agents include but are not limited to quaternary nitrogen-containing compounds that include the following structures: (1) one fatty chain and three lower alkyl (one to four carbon atoms) substituents on the quaternary nitrogen such as stearyltrimethylammonium chloride and cetyldimethylethylammonium bromide; (2) one fatty chain, two lower alkyl groups and a benzyl group such as cetyldimethylbenzylammonium bromide; (3) two fatty chains and two lower alkyl groups such as dimethyldi-(hydrogenated tallow)-ammonium chloride; and the like.

Cationic surface active agents may be present in 100 parts of shampoo in an amount of about 0.1 to about 10 parts by weight, preferably in an amount of about 1 to about 5 parts by weight, and are preferably contained in nonionic, zwitterionic or amphoteric based shampoos.

Exemplary zwitterionic or amphoteric surface active agents include but are not limited to betaines and sultaines such as (a) alkyl betaines where the alkyl group is derived from coconut fatty acids or tallow acids, found in the *CTFA Dictionary* under the names coco-betaine and dihydroxyethyltallow glycinate; (b) alkylamido betaines where the alkyl radical and its bonded carbonyl group are preferably derived from a saturated ($C_{12}$–$C_{18}$) fatty acid, found in the *CTFA Dictionary* under the names lauramidopropyl betaine, myristamidopropyl betaine, stearamidopropyl betaine and cocamidopropylbetaine; (c) sulfobetaines derived from ($C_{12}$–$C_{18}$) fatty acids found in the *CTFA Dictionary* under the names cocamidopropylhydroxysultaine, and oleamido propylhydroxy sultaine; and (d) the alkyl sultaine derived from a $C_{18}$ fatty acid found in the *CTFA Dictionary* under the name coco-sultaine.

Further illustrative amphoterio surfaoe active agents include but are not limited to fatty ($C_{10}$–$C_{18}$) chain amphocarboxylates found under the names cocoamphocarboxypropionate, cocoamphocarboxypropionic acid, cocoamphocarboxypropylsulfonate, cocoamphoglycinate, cocoamphopropionate, cocoamphocarboxyglycinate and cocoamphopropylsulfonate in the *CTFA Dictionary* and *Bench Reference*. Also included among the amphoteric surface active agents are: N-($C_{12}$–$C_{18}$) alkyl mono- or di-propionates, such as sodium laurimino-dipropionate, disodium-N-tallow-beta-iminodipropionate, disodium-N-lauryl-beta-imino-dipropionate and N-lauryl, myristyl-beta-aminopropionic acid, N-coco-beta-aminopropionic acid and sodium-N-coco-beta-aminopropionate; a fatty derivative of glycine, such as laurylaminopropylglycine, and a fatty derivative of asparagine, such as an N, N-dialkylaminoalkyl- N-2 alkyl asparagine wherein the alkyl group contains from about 1 to about 22 carbon atoms.

Useful amounts of zwitterionic or amphoteric surface active agents present in 100 parts of shampoo are typically from about 0.5 to about 25 parts by weight, preferably from about 0.5 to about 10, more preferably from about 0.5 to about 5 parts by weight.

The substantially anhydrous nonionic surface active agents described hereinbefore as useful solubilizing agents may be optionally included among the cleansing surface active agents when they are not being utilized as the solubilizing agent of this invention.

It is to be understood that a nonionic surface active agent that is normally supplied at less than 90 percent active in aqueous solution is suitable for use as part of the total amount of cleansing surface active agent in shampoos of this invention, but is not suitable for use as the substantially anhydrous solubilizing agent for the pearlescing agent as hereinbefore defined.

Further useful cleansing nonionic surface active agents typically available as aqueous solutions include fatty acid esters of sorbitol, fatty acid esters of sucrose, and nonionic compounds having a cationic character, such as the fatty ($C_{12}$-$C_{18}$) tertiary amine oxides, such as dimethylcocoamine oxide and dimethylstearylamine oxide. Useful amounts of nonionic surface active agents present per 100 parts of shampoo may be about 0.5 to about 25 parts by weight, preferably about 1 to about 10 parts by weight.

A shampoo of this invention can be prepared by providing a liquid medium and admixing therein from between about 0.1 to about 20 parts by weight pearlescing base per 100 parts of shampoo, preferably from between about 0.1 to about 15 parts by weight, more preferably from between about 0.2 to about 5 parts by weight pearlescing base in the manner described for the Indirect method of this invention hereinbelow in the method section A.

The shampoo compositions of this invention can be utilized as prepared with the previously mentioned components. However, a further thickening, viscosity-building agent may be added to the shampoo to adjust the viscosity to a range of between about 500 to about 15,000 centipoises measured at 80° F. (about 28° C.), and more preferably to between about 2000 to about 10,000 centipoises.

Preferred viscosity-building agents include cellulosic thickeners, such as a water-dispersible alkyl and hydroxyalkyl substituted polysaccharide wherein the alkyl substituent is selected from the group consisting of methyl and ethyl, and the hydroxyalkyl substituent is selected from the group consisting of 2-hydroxyethyl, 2-hydroxypropyl and 2-hydroxybutyl; and salt, such as sodium chloride or ammonium chloride.

In preferred practice, the viscosity-building ingredient is a cellulose derivative containing methyl and 2-hydroxypropyl substituents on the anhydroglucose rings of the cellulose, hereinafter referred to as the "cellulosic thickener."

Several preferred cellulosic thickeners are available commercially. Particularly preferred among these thickeners are the cellulose derivatives sold under the trademark METHOCEL J Series and METHOCEL E Series by the Dow Chemical Company. For example, METHOCEL J5MS is reported by its manufacturer to contain about equal amounts of methyl and 2-hydroxypropyl substituents on the anhydroglucose rings. METHOCEL E4M is reported to have methyl groups on about 80 to 95 percent of the ring substituents, with hydroxypropyl groups constituting the remaining ring substituents.

The particularly preferred cellulosic thickening agent is utilized in an amount of about 0.25 to about 1.5 parts by weight per 100 parts of the shampoo composition. More preferably, this thickener is present at about 0.5 to about 1 weight percent.

The specific amount of viscosity-building salt that is useful for a shampoo of this invention is a function of the selection and amount of the particular ingredients present as well as of the desired shampoo viscosity. However, the adjustment of viscosity by admixture of salts is also well known and within the skill of those used to preparing shampoos.

The pH value of the compositions of this invention may be in a range of from between about 4 to about 9, preferably from between about 5 to about 7, more preferably from between about 6.0 to about 6.5.

Additional ingredients such as coloring agents, perfumes, preservatives, cosmetic oils, polymers, heavy metal sequestrants and the like can also be incorporated into the shampoo of this invention for their generally recognized purposes.

Briefly described, in the Indirect method of this invention, the pearlescing base is prepared separate and apart from the main body of the shampoo. The pearlescing base is prepared by blending and solubilizing at least one fatty acid ester pearlescing agent with at least one solubilizinq agent. Pearlescence can be obtained by utilizing more than one fatty acid ester in the pearlescing base as a matter of convenience and economy.

This is accomplished by heating the solubilizing agent to a temperature above the melting point of the fatty acid ester utilized and below the boiling point of the solubilizing agent. Where two or more fatty acid esters are utilized, the solubilizing agent is heated to the melting point of the highest melting fatty acid ester present in the mixture of esters. While the solubilizing agent is so heated and in a liquid state, as where a wax-like solid solubilizing agent is used, the fatty acid ester is blended with the solubilizing agent and dispersed therein until the ester is solubilized. The resulting presolubilized pearlescing agent solution is referred to herein as the pearlescing base. The pearlescing base is provided at a temperature above the melting point of the fatty acid ester for admixture with the liquid medium.

The liquid medium of the shampoo that contains the water and surface active cleansing agent is prepared by conventional techniques. The liquid medium is provided at a temperature, prior to admixing the pearlescing base therein, above the melting point of the fatty acid ester present in the pearlescing base and below the boiling point of the liquid medium. Persons skilled in the art will recognize that the melting points of esters and solubilizing agents useful herein are not precise.

The shampoo composition is prepared by admixing the heated pearlescing base into the heated liquid medium, while maintaining the temperature of the admixture above the melting point of the fatty acid ester, or above the highest melting point of the highest melting fatty acid ester in a mixture of such esters and below the boiling point of the lowest boiling ingredient.

Once the liquid pearlescing base and liquid medium are admixed, the resulting admixture is agitated until it is substantially homogeneous and substantially transparent to visible light. It is thought that the observed shampoo transparency is due to the formation of a solution of the presolubilized ester, or a dispersion of very finely divided liquid crystalline pearlescing agent being formed in the liquid medium at this stage of the method.

The temperature of the transparent admixture is thereafter gradually reduced to a temperature lower than the melting point of the fatty acid ester pearlescing agent or lowest melting fatty acid ester present to form the pearlescent shampoo. A gradual temperature reduction is thought to lead to crystallization of the ester and its suspension therein in a crystalline state to effect the observed pearlescence.

Optionally, the pearlescing base may be prepared as previously described, and thereafter cooled to ambient room temperature and stored as a pearlescing base concentrate for use in a future shampoo batch or in a cosmetic emulsion, such as skin care lotions, creams or gels or in hair care products, such as hair waving and hair setting lotions, and the like. It must, however, be reheated to a liquid state as described above, prior to use.

It is noted that when pearlescent shampoos are prepared by a conventional direct method, such as that of my before-described U.S. patent, crystallization of the pearlescing agent normally leads to precipitation or phase separation of the crystals so produced. Here, however, cooling and presumed crystallization typically does not lead to phase separation of the crystalline fatty acid ester pearlescing agent from the liquid medium, unless the ratio of solubilizing agent is less than about 4 parts by weight per part of ester. However, the particularly preferred cellulosic thickeners described hereinbefore can also stabilize the pearlescent shampoo and retard the phase separation of compositions outside the preferred range, as noted in my before-described patent.

In a conventional "direct" method of preparing a pearlescent shampoo, the pearlescing agent is typically added, preferably in a molten form, directly to the main body of the shampoo. Typical amounts used are between 1 and 2 weight percent of the shampoo and those amounts are added at a temperature above the melting point of the pearlescing agent.

Other ingredients, such as perfumes, coloring agents, pH adjusting agents and preservatives typically included in a shampoo are normally added to the product after it has been cooled to a temperature below about 50° C. (about 122° F.), preferably below about 45° C. (about 113° F.). As a practical matter, it is also prudent to wait until this step of the process to make any adjustments in the pH value of the product, because certain commonly used surface active agents may be easily hydrolyzed at acidic pH values and/or at elevated temperatures.

Shampoo compositions prepared by the method of this invention consistently develop an attractive, excellent, aesthetically elegant pearlescence that has an iridescent-like quality when the composition is shaken, stirred, swirled or otherwise similarly disturbed. Pearlescence was noted within an aging period of about five days, preferably within a period of about four days, more preferably within a period of about three days.

Additionally, it was surprisingly noted that once optimum pearling takes place in a shampoo of this invention, the viscosity remains thereafter substantially unchanged.

A further surprising finding is that the period within which substantial pearling takes place can be further accelerated to within 24 hours. This is accomplished by dispersing therein a low level of a crystalline pearlescence accelerating agent to the heated admixture immediately prior to reducing the temperature of the admixture below the melting point of the fatty acid ester pearlescing agent. The pearlescence accelerating agent is added to the admixture while the latter is at a temperature above the melting point of the fatty acid ester present in the pearlescing base as described earlier.

Useful pearlescence accelerating agents include, but are not limited to, glycol mono- and di-esters of $(C_{12}-C_{22})$ fatty acids, and $(C_2-C_4)$ alkylene glycol esters of $(C_{12}-C_{22})$ fatty acid, magnesium stearate, zinc stearate and the like. The pearlescence accelerating agent is preferably present in a crystalline state when it is included in the heated shampoo.

Useful amounts of pearlescence accelerating agent are in the range of from between about 0.01 to about 0.2 parts by weight, preferably from between about 0.05 to about 0.1 parts by weight per 100 parts of the shampoo. A particularly preferred pearlescence accelerating agent is ethylene glycol monostearate.

Pearlescence accelerating agents as described hereinabove may be used when time constraints require a speedier preparation of shampoo for shipping or when equipment usage priority demands are high.

The mechanism by which the pearlescence accelerating agent operates is also not fully understood. In the absence of the fatty acid ester in the pearling base of this invention, the preferred pearlescence accelerating agent, which is itself a known pearlescing agent, does not induce pearlescence. Nevertheless, when used in the non-pearlescing amounts described before, the pearlescence accelerating agent enhances the pearling effect.

The present invention is further illustrated in the examples that follow.

BEST MODE FOR CARRYING OUT THE INVENTION

A. Method for Preparinq Pearlescent Shampoo

In the Examples that follow hereinbelow, reference will be made to a method of preparing a pearlescent shampoo of this invention, hereinafter "Indirect" method, and to a conventional method, hereinafter "Direct" method. For convenience, the detailed procedural steps of these methods are illustrated below for a typical shampoo composition of this invention.

Shampoo Ingredients in order of addition Liquid Medium

1. Water
2. Viscosity increasing agent (gum, salt thickeners)
3. Heavy metal sequestering agent
4. Cleansing surface-active agents (anionic, nonionic, zwitterionic, cationic or mixture thereof)

Pearlescing Base (Indirect Method)

5. Substantially anhydrous solubilizing agent for fatty acid ester pearlescing agent (absent in Direct Method)
6. fatty acid ester (or mixture thereof) pearlescing agent Other ingredients 7. Preservatives
8. Perfume (colorants, if desired)
9. pH adjusting agent to a value of about 4 to about 9, preferably from about 5 to about 7, more preferably from about 6.0 to about 6.5.

Indirect Method of Preparing Pearlescent Shampoo (a) In one container, provide a liquid medium containing ingredient #1, heat to about 40° C. (about 104° F.), and add while dispersing with mechanical stirring in the following order, ingredients #2, #3, and #4.

(b) Heat the liquid medium provided in step (a) to about 60° C. (about 140° F.).

(c) In a second container provide a pearlescing base by adding ingredient #5 to the second container, heating it to a temperature of about 60° C. (about 140° F.) and maintaining it at said temperature. Presolubilize ingredient #6 blending it with the heated ingredient #5 in the second container. (Ingredient #6 may either be premelted or added in the form of a solid as convenient). Mechanical stirring may be utilized if desired. The solubilization period lasts until ingredient #6 is substantially solubilized and the pearlescing base so formed is homogeneous. (When ingredient #5 is a mono- or a di-alkanolamide of a fatty acid, this heated solubilization step is preferably carried out in a time period of less than 2 hours to avoid ester hydrolysis.)

(d) Admix the heated pearlescing base provided in step (c) under mechanical stirring with the heated liquid medium provided in step (b) in the first container.

(e) Maintain the temperature of the admixture provided in step (d) at a temperature of about 60° C. (about 140° F.) for a period of about 10 minutes or until the admixture is substantially homogeneous and substantially transparent to visible light.

(f) Cool the admixture provided in step (e) to a temperature of about 50° C. (about 122° F.).

(g) Add to the admixture provided in step (f), and disperse with mechanical stirring in the following order, ingredients #7, #8 and #9 to provide a shampoo.

(h) Cool the shampoo provided by step (g) to ambient room temperature and transfer the product to a transparent container for aging storage.

(i) Measure the viscosity of a freshly prepared shampoo sample in centipoises using the well-known rotational Brookfield Viscometer at a temperature of about 26° C. (about 80° F.) and record the values.

(j) Examine the appearance of the freshly prepared shampoo and record the pearlescence level.

(k) Repeat steps (i) and (j) at periodic intervals during a period of aging storage and compare against the initially recorded observation.

Direct Method of Preparing Pearlescent Shampoo (a) In one container, provide a liquid medium containing ingredient #1, heat to about 40° C. (about 104° F.), and add, while dispersing with mechanical stirring, in the following order ingredients #2, #3 and #4 (and #5, if ingredient #5 is also a cleansing surface-active agent).

(b) Follow the procedure in step (b) of the Indirect method.

(c) Add ingredient #6 to the heated liquid medium provided in step (b) in either solid form or in pre-melted form as convenient.

(d) Follow the procedural steps (e)–(k) of the Indirect method.

EXAMPLE 1

Pearlescent Shampoos

This Example illustrates the benefits of preparing a pearlescent shampoo composition using the Indirect method of this invention compared to using the Direct method. The procedure of each method described in the foregoing Section A was followed.

A shampoo formula labeled "A" was prepared with varying amounts of fatty acid ester present in the pearlescing base. For purposes of illustrating the invention, a fatty acid alkanolamide, N, N-bis-(2-hydroxyethyl)-coco fatty acid amide, was selected as the substantially anhydrous solubilizing agent.

This solubilizing agent, like the other ingredients, was commercially available from a number of well-known suppliers found in the previously discussed CTFA Dictionary and Bench Reference.

The formula for shampoo "A" follows. For convenience, the ingredients are numbered to correspond with those of the typical shampoo composition described above in method Section A.

| Formula A | | |
|---|---|---|
| Shampoo Ingredients | | Parts By Weight (as is) |
| Liquid Medium | | |
| 1. | Water to 100 parts by weight | Q.S. |
| 2. (a) | Cellulose Thickener* | 0.6 |
| 2. (b) | Ammonium chloride | 0.5 |
| 3. | Tetrasodium ethylenediaminetetraacetic acid (39 percent active) | 0.2** |
| 4. (a) | Ammonium lauryl sulfate (30 percent active) | 36.0** |
| 4. (b) | Cocamidopropylhydroxysultaine*** (40 percent active) | 1.5** |
| Pearlescing Base | | |
| 5. | N, N—bis-(2-hydroxyethyl) coco fatty acid amide**** | 2.5** |
| 6. | Fatty acid ester | 0.2–0.5 |
| Other Ingredients | | |
| 7. | Preservative | Q.S. |
| 8. | Perfume | Q.S. |
| 9. | Citric acid (50 percent in water) added to pH 6.1–6.3 | Q.S. |

*The cellulose thickener was a hydroxypropylmethylcellulose sold under the trademark METHOCEL J5MS by the Dow Chemical Company, Midland, MI.
**Active parts by weight present in the finished shampoo were 0.078 for ingredient #3, 10.8 for ingredient #4 (a) and 0.6 for ingredient #4 (b)
***Available commercially under the trademark VARION CAS supplied by Sherex Chemical Company, Inc., Dublin, OH.
****An extensive listing of suppliers is found under the name Cocamide DEA in the CTFA Dictionary, and cocoyl diethanolamide in the Bench Reference.

A series of shampoos was prepared by the Indirect method (I) replacing the water in formula A by successive amounts of one of the fatty acid esters identified hereinbelow. The concentration of ester was varied from about 0.1 to 0.5 parts by weight ester to provide a ratio in the range of from about 4 to about 15 parts by weight of amide per parts of ester. A second similar series of shampoos using the same ester was prepared by the Direct method (D) except that ingredient #5 was included in the liquid medium along with ingredients #4(a) and #4(b). The foregoing sequence was followed for each member of the following homologous series of fatty acid esters. For comparison, Formula A was also prepared without any fatty acid ester.

| ESTER | LENGTH OF FATTY CHAIN | MELTING POINT °C. | °F. |
|---|---|---|---|
| Myristyl Myristate (MM) | C14—C14 | 37–38 | 98–100 |
| Myristyl Palmitate (MP) | C14–C16 | 44–46 | 111–115 |
| Myristyl Stearate (MS) | C14–C18 | 45–46 | 113–115 |
| Cetyl Myristate (CM) | C16–C14 | 47–49 | 116–120 |

| ESTER | LENGTH OF FATTY CHAIN | MELTING POINT °C. | °F. |
|---|---|---|---|
| Cetyl Palmitate (CP) | C16—C16 | 48–50 | 118–122 |
| Cetyl Stearate (CS) | C16–C18 | 48–50 | 118–122 |
| Stearyl Myristate (SM) | C18–C14 | 47–49 | 116–120 |
| Stearyl Palmitate (SP) | C18–C16 | 54–56 | 129–132 |
| Stearyl Stearate (SS) | C18—C18 | 53–55 | 125–131 |

The results noted for each fatty acid ester are summarized in the Table below along with viscocity data and comments about pearlescence. The Brookfield viscocity of the freshly prepared shampoo was measured in centipoises (initial cps value), and at periodic intervals during the aging of the stored shampoo. The "final" viscosity value, therefore, denotes the value after which the measured viscosity remained substantially unchanged, and the period of aging relating thereto.

| Series No. | Ester | Parts by Weight* | Method I | Method D | Viscosity (cps) Initial | Viscosity (cps) Final | Pearlescence |
|---|---|---|---|---|---|---|---|
| (1) | MM | 0.3–0.4 | X | — | 2300 | 4200 (2 wks) | within 1–2 wks |
| (2) | MM | 0.3–0.4 | — | X | 1500 | 5500 (1 wk) | within 1–3 days |
| (3) | MP | 0.2–0.4 | X | — | 3000 | 7000 (1–2 days) | within 1–4 days |
| (4) | MP | 0.2–0.4 | — | X | 6300 | 6800 (1 wk) | None, 1–4 days (Notes a, b) |
| (5) | MS | 0.2–0.4 | X | — | 3000 | 7000 (1–2 days) | within 1–4 days, (Note c) |
| (6) | MS | 0.2–0.4 | — | X | 7000–8500 | 7000–8500 (4 wks) | none to very slight, 4 wks, (Note b) |
| (7) | CM | 0.2–0.4 | X | — | 3000 | 7000 (1–2 days) | within 1–4 days, (Note c) |
| (8) | CM | 0.2–0.4 | — | X | 7000–8500 | 7000–8500 (4 wks) | none to very slight, 4 wks |
| (9) | CP | 0.2–0.4 | X | — | 3000 | 7000 (1–2 days) | within 1–4 days, (Note c) |
| (10) | CP | 0.2–0.4 | — | X | 7000–8500 | 7000–8500 (4 wks) | none to very slight, 4 wks |
| (11) | CS | 0.2–0.4 | X | — | 3000 | 7000 (1–2 days) | within 1–4 days, (Note c) |
| (12) | CS | 0.2–0.4 | — | X | 7000–8500 | 7000–8500 (4 wks) | none to very slight, 4 wks |
| (13) | SM | 0.2–0.4 | X | — | 3000 | 7000 (1–2 days) | within 1–4 days, (Note c) |
| (14) | SM | 0.2–0.4 | — | X | 7000–8500 | 7000–8500 (4 wks) | none to very slight, 4 wks, (Note b) |
| (15) | SP | 0.2–0.4 | X | — | 3000 | 7000 (1–2 days) | within 1–4 days, (Note c) |
| (16) | SP | 0.2–0.4 | — | X | 7000–8500 | 7000–8500 (4 wks) | none to very slight, 4 wks |
| (17) | SS | 0.2–0.4 | X | — | 3000 | 7000 (1–2 days) | within 1–4 days, (Note c) |
| (18) | SS | 0.2–0.4 | — | X | 7000–8500 | 7000–8500 (4 wks) | none to very slight, 4 wks, (Note b) |

*When the parts by weight of ester per 100 parts of shampoo were below the lower limit shown, the level of pearlescence noted was less attractive in shampoos prepared by the Indirect method, and no pearlescence was noted in shampoos prepared by the Direct method. When the parts by weight exceeded the upper limit shown, i.e., about 0.45 –0.50, the pearling process took about 1 day longer than the period noted for shampoos prepared by the Indirect method, and phase separation was noted within a period of 7 days in shampoos prepared by the Direct method.
Note a.
A medium level of pearlescence developed within 1 week.
Note b.
Slight phase separation took place at week.
Note c.
Pearl is elegant and stable.

The tabulated results show that a pearlescent shampoo having an attractive, elegant, stable pearl was consistently produced when the Indirect method of this invention was used. The results further show that myristyl myristate, MM, while useful in the method of this invention developed pearlescence slowly when the Indirect method was used. MM was again found singularly more suitable as a pearlescing agent when the more conventional Direct method was used. This behavior was in keeping with the teachings of my patent discussed hereinbefore.

The results of the Indirect method further show that an elegant stable pearl was produced within a commercially practical period of less than 5 days, when the amount of fatty acid ester, except for MM, fell within a range of from about 0.2–0.4 parts by weight per 100 parts of shampoo. MM, on the other hand, required the Direct method, and a lower limit above 0.2 parts by weight per 100 parts of shampoo to produce suitable pearlescence within the same period of time.

Based on the elegant appearance of the pearlescence achieved within a period of within 4 days using the Indirect method, the preferred parts by weight ratio of ester:amide (the solubilizing agent used herein) fell in the range of from between about 1:4 to about 1:15. The pearlescence obtained was elegant in that it had a highly refractive, iridescent quality, particularly when the shampoo composition was shaken, stirred, swirled or otherwise similarly disturbed.

A further finding was that the foaming and lathering properties of the pearlescent shampoos prepared by the Indirect method were substantially the same as those of Formula A similarly prepared without the fatty acid ester present. The amide used is a generally recognized foam booster.

This result showed that a pearlescing agent, prepared as disclosed herein using a known amide foam booster as the solubilizing agent had no negative effect on either its cosmetic functionality, or on the overall performance expected of a shampoo composition in terms of foaming, cleansing and lathering normally associated therewith.

An even further finding was that the presolubilized fatty acid ester pearlescing agent prepared in the manner described herein remained suspended in a crystalline state. Thus, the ester was suspended in the shampoo to produce pearlescence without being dissolved by the cleaning surface active agents of the liquid medium, a problem commonly encountered.

EXAMPLE 2

Pearlescent Shampoos

The formula for Shampoo "A" of Example 1 was utilized in this study, except that the solubilizing agent used was the fatty alkanolamide, N-(2-hydroxyethyl) coco fatty acid amide supplied under the trademark MONAMID CMA by Mona Industries, Inc., Paterson, N.J.

This amide is commercially available from a number of other suppliers found under the CTFA adopted name of Cocamide MEA in the *CTFA Dictionary*, and under the name cocoyl monoethanolamide in the *Bench Reference*.

A series of shampoos were prepared following the procedure of Example 1 by the Indirect method only, using each of the fatty acid esters of Example 1, except MM.

An excellent stable pearl was produced within an aging period of about four days at a fatty acid ester content of from about 0.2–0.4 parts by weight per 100 parts of shampoo. The initial Brookfield viscosity value was in the range of between about 1500 to 2000 cps. The final viscosity was in the range of between about 5000 to about 7000 cps and remained substantially unchanged thereafter.

EXAMPLE 3

Pearlescent Shampoo

The formula for shampoo "A" of Example 1 was again utilized, except that the solubilizing agent used was the amide, N, N-bis-(2-hydroxyethyl)lauramide supplied under the trademark NINOL AA 62 EXTRA by the Stepan Company, Northfield, IL.

This amide is commercially available from a number of other suppliers found under the CTFA adopted name of lauramide DEA in the *CTFA Dictionary*, and under the name of lauroyl monoethanolamide in the *Bench Reference*.

A series of shampoos were prepared following the procedure of Example 1 by the Indirect method only, using each of the fatty acid esters of Example 1, except MM.

An excellent stable pearl was produced within an aging period of about four days at an ester content of from about 0.2–0.4 parts by weight per 100 parts of shampoo. The initial Brookfield viscosity value was in the range of between about 2000 to 3000 cps. The final viscosity was in the range of between about 6000 to about 7000 cps and remained substantially unchanged thereafter.

EXAMPLE 4

Pearlescent Shampoos

The formula for shampoo "A" of Example 1 was again utilized, except that the cellulose thickener, Ingredient #2(a), and one of the surface active agents, Ingredient #4(b), were omitted. The omitted ingredients were replaced by increasing the content of the remaining surface agent, Ingredient #4(a), accordingly. A series of shampoos were prepared following the procedure of Example 1 by the Indirect method using each of the fatty acid esters, except MM.

An excellent stable pearl was produced within an aging period of about four days at an ester content of from about 0.2–0.4 parts by weight per 100 parts of shampoo. The initial Brookfield viscosity value was in the range of between about 1400 to 1600 cps. The final viscosity was in the range of between about 3500 to about 4000 cps and remained substantially unchanged thereafter.

EXAMPLE 5

Pearlescent Shampoos

This Example compares three pearlescent shampoos prepared by the Indirect method with their counterparts prepared by the Direct method. The shampoo formula "A" of Example 1 was utilized except for the fatty acid ester and amounts used as shown in the following table.

| Ester | Parts by Weight | Method I | Method D | Ratio* Ester:Amide | Pearlescence (1–4 days) |
|---|---|---|---|---|---|
| MP | 0.40 | X | — | 1:6.25 | Excellent |
|  |  | — | X | 1:6.25 | None, opaque |
| CP | 0.30 | X | — | 1:8.33 | Excellent |
|  |  | — | X | 1:8.33 | Medium |
| SS | 0.20 | X | — | 1:12.5 | Excellent |
|  |  | — | X | 1:12.5 | None, opaque |

*amide content = 2.5 parts by weight active per 100 parts shampoo.

The above results showed that an attractive, excellent stable pearl developed with a ratio of between about 6 to about 13 parts by weight of amide per parts of ester. These results also show that pearlescent shampoos were consistently produced even at low levels of 0.2 parts by weight fatty acid ester pearlescing agent per 100 parts of shampoo.

EXAMPLE 6

Pearlescent Shampoos

This Example illustrates the superiority of the Indirect method of this invention over the Direct method in consistently producing pearlescent shampoos.

The formula for Shampoo "A" of Example 1 was utilized, using myristyl stearate at a concentration of 0.4 parts by weight as the fatty acid ester pearlescing agent. The shampoo was prepared by the Indirect method and by the Direct method. The results are compared below.

|  | Indirect Method | Direct Method |
|---|---|---|
| Viscosity (cps) |  |  |
| Initial | 2700 | 5500 |
| Final (3 days) | 6200 | 6300 |
| Appearance at Ambient Temperature |  |  |
| Initial | slightly hazy | opaque |
| After 1 day | slight pearl | opaque, no pearl |
| After 3 days | elegant pearl | no pearl |
| After 1 week | unchanged | slight pearl, noticeable phase separation |
| After 6 months | stable, no | — |

| | Indirect Method | Direct Method |
|---|---|---|
| | phase separation | |

The above results show that elegant pearlescence developed within 3 days an the appearance remained substantially unchanged in the shampoo prepared by the Indirect method. On the other hand, the shampoo prepared by the Direct method was judged a failure owing to phase separation, and poor pearl development.

EXAMPLE 7

Pearlescent Shampoos

This Example illustrates the usefulness of various anionic and amphoteric surface active agents frequently utilized in shampoos for their cleansing effectiveness.

The formula for Shampoo "A" of Example 1 was used, except that the level of cleansing surface active agent (Ingredient #4) was varied from between about 9 to about 15 parts by weight, active basis per 100 parts of shampoo, in a series of shampoos prepared by the Indirect method using MS as ingredient #6 in an amount of 0.4 parts by weight per 100 parts of shampoo.

The following series of shampoos were prepared, labeled 1 to 7, using the weight ratio of ester:amide represented in the pearlescing base as shown in the Table below.

| Shampoo | Surface active agent | Active Parts by Weight | Ratio Ester: Amide |
|---|---|---|---|
| (1) | Sodium lauryl sulfate | 11.1 | 1:7 |
| (2) | Sodium olefin (C14–C16) sulfonate (note a) | 12.8 | 1:6 |
| (3) | Ammonium laureth sulfate (note b) | 11.1 | 1:6 |
| (4) | Sodium laureth sulfate (note c) | 11.1 | 1:6 |
| (5) | Triethanolamine lauryl sulfate (note d) | 16.0 | 1:6 |
| (6) | Sodium N—cocoyl-sarcosinate (note e) | 9.6 | 1:8 |
| (7) | Cocoamphocarboxy-glycinate (note f) | 14.0 | 1:7 |

All of the shampoos had an elegant pearlescence within a period of about one to four days.
Note a.
CTFA adopted name for a mixture of long chain sulfonate salts prepared by the sulfonation of $C_{14}$-$C_{16}$ alpha olefins, available under the trademark BIO TERGE AS-40 from the Stepan Company, Northfield, IL, as a 40 percent solution in water
Note b.
CTFA adopted name for the ammonium salt of ethoxylated ammonium lauryl sulfate containing an average of between 1 and 4 ethylene oxide units per molecule, available under the trademark CARSONOL ALES-4 from Lonza, Inc., Fairlawn, NJ, as a 30 percent solution in water.
Note c.
CTFA adopted name for sodium polyoxyethylene lauryl sulfate containing an average of between 1 and 4 oxyethylene units per molecule, available under the trademark CARSONOL SLES from Lonza, Inc., Fairlawn, NJ, as a 30 percent solution in water.
Note d.
Available commercially as a 30 percent solution in water, sold under the trademark CARSONAL TLS by Lonza, Inc., Fairlawn, NJ.
Note e.
Available commercially as a 30 percent solution in water, sold under the trademark HAMPOSYL C-30 by W. R. Grace & Co., Lexington, MA.
Note f.
CTFA adopted name for an amphoteric surfactant corresponding to CAS #68650-39-5 derived from substituted imidazolines having a terminal group derived from coconut fatty acid, available commercially under the trademark MIRANOL C2M from the MiranolChemical Co., Inc., Dayton, NJ, as a 40 percent solution in water.

Shampoo compositions, No. 1–7, all developed an elegant pearlescene within a period of about 1 to 4 days.

EXAMPLE 8

Pearlescent Shampoo

This Example compares a pearlescent shampoo of this invention prepared following the Indirect method to a shampoo prepared by the Direct method described in Section A above. The pearlescing base is comprised of stearyl palmitate, as the pearlescing agent and polyoxyethylene (9)nonylphenyl ether, a nonionic surface active agent, as the solubilizing agent at a weight ratio of about 10 parts by weight solubilizing agent per part of ester.

| Ingredient | Active Parts by Weight |
|---|---|
| Liquid Medium | |
| 1. Water to 100 parts by weight | Q.S. |
| 2. Ammonium chloride | 1.2 |
| 3. Sodium lauryl sulfate* | 12.0 |
| Pearlescing Base | |
| 4. Stearyl palmitate | 0.3 |
| 5. Polyoxyethylene (9) nonyl phenyl ether** | 3.0 |
| Other Ingredients | |
| 6. Preservative | Q.S. |
| 7. Perfume | Q.S. |
| 8. Citric acid (50 percent active) to pH 6.1–6.3 | Q.S. |

*An extensive listing of suppliers is found under this name in the CTFA Dictionary and in the Bench Reference.
**Available commercially under the trademark IGEPAL CO-630 supplied by the GAF Corporation, Wayne, NJ. An extensive listing of other suppliers is also found under the name, nonoxynol-9 in the CTFA Dictionary and in the Bench Reference.

The results are compared below.

| | Indirect Method | Direct Method |
|---|---|---|
| Viscosity (cps) | | |
| Initial | 850 | 2600 |
| After 1 day | 1300 | 2700 |
| Final (4 days) | 2950 | 2700 |
| Appearance at Ambient Temperature | | |
| Initial | slightly hazy | opaque |
| After 1 day | slight pearl | no pearl |
| After 4 days | elegant pearl | no pearl |

The above results show the superiority of the Indirect method in consistently producing a pearlescent shampoo with the pearlescing agent of this invention.

EXAMPLE 9

Pearlescent Shampoo

This Example compares a pearlescent shampoo of this invention prepared by the Indirect method to a shampoo prepared by the Direct method described in Section A above. The pearlescing base is comprised of cetyl palmitate and the fatty alkanolamide of Example 1 (Ingredient #5) as the solubilizing agent at a ratio of about 8.5 parts by weight solubilizing agent per part of ester.

| Ingredient | Parts by Weight |
|---|---|
| Liquid Medium | |
| 1. Water to 100 parts by weight | Q.S. |
| 2. Cellulosic thickener of Example 1, Shampoo A. | 0.5 |
| 3. Ammonium chloride | 1.0 |
| 4. Tetrasodium ethylenediamine-tetraacetic acid (50 | 0.2* |

-continued

| Ingredient | Parts by Weight |
|---|---|
| percent active in water) | |
| 5. Ammonium lauryl sulfate (30 percent active) | 25.0* |
| 6. Sodium laureth sulfate** (30 percent active) | 15.0* |
| Pearlescing Agent | |
| 7. Cetyl palmitate | 0.7 |
| 8. N, N—bis-(2-hydroxyethyl) coco fatty acid amide (Ingredient #5 of Example 1, basic formula A) | 6.0 |
| Other Ingredients | |
| 9. Preservative | Q.S. |
| 10. Perfume | Q.S. |
| 11. Citric acid (50 percent active) to pH 6.1–6.3 | Q.S. |

*actual active parts by weight = 0.1 for ingredient #4; 7.5 for ingredient #5 and 4.5 for ingredient #6.
**See note c of Example 7.

The results are compared below.

| | Indirect Method | Direct Method |
|---|---|---|
| Viscosity (cps) | | |
| Initial | 3,500 | 14,000 |
| After 2 days | 16,500 | 15,000 |
| Appearance at Ambient Temperature | | |
| Initial | slightly hazy | opaque |
| After 2 days | elegant pearl | no pearl |

The above results again show the superiority of the Indirect method of this invention over the Direct method in consistently producing a pearlescent shampoo.

EXAMPLE 10

Pearlescent Shampoo

This Example illustrates the utility of a polyethylene glycol ether of a fatty alcohol as the substantially anhydrous solubilizing agent of this invention. These materials are commercially available as a homologous series of ($C_{12}$–$C_{18}$) fatty alcohols typically having an average of about 2 to about 21 oxyethylene units per molecule. Particularly useful materials are supplied by ICI Americas, Inc. under the BRIJ ® trademark series.

The formula for Shampoo "A" of Example 1 was utlized in this study except that the pearlescing base was comprised of 3 parts by weight Brij ® 30 (containing an average of 4 oxyethylene units per molecule), and 0.4 parts by weight cetyl palmitate per 100 parts of shampoo. This represented a ratio of about 7.5 parts by weight solubilizing agent per parts ester.

The shampoo was prepared by the Indirect method, and the resulting product developed an elegant pearl within an aging period of about 4 days.

EXAMPLE 11

Pearlescent Shampoos

This example illustrates the use of mixtures of fatty acid esters in the pearlescing base for shampoos prepared by the Indirect method. The formula for shampoo formula "A" of Example 1 was used, except that the pearlescing base was comprised of a mixture of two fatty acid ester pearlescing agents, as shown below, and Ingredient #5 of Formula "A", Example 1 as the anhydrous solubilizing agent.

| Pearlescing Agent Ingredients | Parts by Weight Formula | |
|---|---|---|
| | 1 | 2 |
| Myristyl stearate | 0.2 | — |
| Stearyl stearate | 0.1 | — |
| Cetyl palmitate | — | 0.2 |
| Stearyl myristate | — | 0.2 |
| N, N—bis-(2-hydroxyethyl) coco fatty acid amide (Ingredient 5 of Example 1, formula A) | 2.5 | 3.0 |

The respective weight ratio of ester to amide in the order listed in Formula 1 is 2:1:25 per 100 parts of pearlescing base representing a weight ratio of total ester to solubilizing agent of 1:8.33 per 100 parts of shampoo. The respective ratio of ester to amide in the order listed in Formula 2 is 1:1:15 per 100 parts of pearlescing base representing a weight ratio of total ester to solubilizing agent of 1:7.5 per 100 parts of shampoo.

The shampoo compositions produced with mixtures of fatty acid esters in the pearlescing base developed an excellent pearl within a period of one to four days.

EXAMPLE 12

Pearlescent Shampoos with Pearlescence Accelerating Agents

This example illustrates the effect of a pearlescence accelerating agent on the pearlescing process of the Indirect method in the absence of and in the presence of a fatty acid ester.

The formula for Shampoo "A" of Example 1 was used, containing 0.4 percent myristyl stearate prepared following the procedure of the Indirect method, except that prior to reducing the temperature of the admixture in step (h), a small amount of about 0.05 to about 0.1 parts by weight per 100 parts of shampoo of ethylene glycol monostearate was added to the hot shampoo admixture. For comparison, a second shampoo was prepared without the fatty acid ester pearlescing agent.

The pearling of the shampoo prepared by the Indirect method was accelerated, and excellent pearlescence was noted within a period of 12 to 24 hours. On the other hand, the shampoo containing no fatty acid ester, developed no pearlescence even after a period of two weeks. This finding was surprising, because ethylene glycol monostearate is itself a known pearlescing agent.

The present invention has been described with respect to preferred embodiments. It will be clear to those skilled in the art that modifications and/or variations of the disclosed compositions and methods can be made without departing from the scope of the invention set forth herein.

What is claimed is:

1. In a method for preparing an improved pearlescent shampoo containing a pearlescent agent that includes the steps of providing a liquid medium containing water and an amount of surface active agent effective for cleansing, which liquid medium is heated to a temperature above the melting point of the pearlescent agent and below the boiling point of the medium; admixing with stirring a pearlescing agent at a temperature above the melting point of said pearlescing agent with said heated liquid medium; maintaining the admixture so formed with stirring above the melting point of said pearlescing agent and below the boiling point of the lowest boiling ingredient in the liquid medium for a time sufficient to form a substantially homogeneous admixture that is substantially transparent to visible light; and thereafter reducing the temperature of said admixture to ambient room temperature to form a shampoo that exhibits pearlescence; the improvement which comprises:

blending and solubilizing a fatty acid ester whose fatty acid portion is derived from a saturated $C_{16}$–$C_{22}$ fatty acid and whose alcohol portion is derived from a $C_{14}$–$C_{22}$ fatty alcohol as the pearlescing agent in a substantially anhydrous nonionic surface active agent as solubilizing agent at a weight ratio of between 1 to about 25 parts of said solubilizing agent per part pearlescing agent to form a substantially homogenous, liquid, anhydrous pearlescing base, said blending and solubilizing being carried out at a temperature above the melting points of both said solubilizing agent and said pearlescing agent and below the boiling point of said solubilizing agent prior to said admixture of said pearlescing agent and said heated liquid medium; and thereafter admixing said heated, substantially homogeneous liquid, anhydrous pearlscing base with said heated liquid medium in an amount to provide about 0.01 to about 2.5 pats by weight of said pearlescing agent per 100 parts by weight of the formed shampoo;

said shampoo so formed exhibiting pearlescence within a time period of about 5 days at ambient room temperature.

2. The method of claim 1 wherein the ratio of said solubilizing agent to said pearlescing agent is about 4 to about 15 parts by weight solubilizing agent per part pearlescing agent.

3. The method of claim 1 wherein the amount of said substantially homogeneous, liquid, anhydrous pearlescing base admixed with said heated liquid is sufficient to provide about 0.01 to about 1.0 parts by weight of pearlescing agent to said shampoo.

4. The method of claim 1 wherein the amount of said substantially homogeneous, liquid, anhvdrous pearlescing base admixed with said heated liquid is sufficient to provide about 0.05 to about 0.8 parts by weight of pearlescing agent to said shampoo.

5. The method of claim 1 including the further step of admixing a $C_2$–$C_4$ alkylene glycol ester of a $C_{12}$–$C_{22}$ fatty acid, as a pearlescence accelerating agent, to the substantially homogeneous admixture formed after admixture of said pearlescing base and said liquid medium and prior to reducing the temperature of said admixture to ambient room temperature, said pearlescene accelerating agent being admixed in a crystalline state and in an amount sufficient to provide about 0.01 to about 0.2 parts by weight per 100 parts by weight of the shampoo.

6. The method of claim 5 wherein said pearlescence accelerating agent is ethylene glycol monostearate.

7. The method of claim 1 wherein said pearlescing base is admixed in an amount of about 0.10 to about 20 parts by weight per 100 parts of the shampoo.

8. The method of claim 1 wherein said pearlescing agent is selected from the group consisting of myristyl palmitate, myristyl stearate, cetyl myristate, cetyl palmitate, cetyl stearate, stearyl myristate, stearyl palmitate, stearyl stearate, stearyl behenate, and mixtures thereof.

9. The method of claim 1 wherein said pearlescing agent is myristyl stearate.

10. The method of claim 1 wherein said solubilizing agent is selected from the group consisting of polyoxy($C_2$–$C_4$)alkylene derivatives of $C_8$–$C_{22}$ fatty alcohols containing from about 1 to about 100 oxyethylene, oxypropylene, and oxyethylene/oxypropylene condensation units per molecule, polyoxyethylene derivatives of $C_8$–$C_{22}$ alkyl phenols containing an average of from about 3 to about 150 oxyethylene units per molecule, copolymers of ethylene oxide and propylene oxide, mono- and di-($C_2$–$C_4$)alkanolamides of $C_8$–$C_{22}$ and mixtures thereof.

11. The method of claim 1 wherein said solubilizing agent is a di-($C_2$–$C_4$)-alkanolamide of a $C_8$–$C_{22}$ fatty acid present in an amount of from about 0.01 to about 15 parts by weight per 100 parts of the shampoo.

12. The method of claim 11 wherein said alkanolamide solubilizing agent is N,N-bis-(2-hydroxyethyl) coco fatty acid amide.

13. The method of claim 1 wherein said substantially homogeneous, liquid, anhydrous pearlescing base is comprised of myristyl stearate, strearyl stearate and said solubilizing agent is present in a respective weight ratio of 2:1:25 parts by weight per 100 parts of said pearlescing base.

14. The method of claim 1 wherein said substantially homogeneous, liquid, anhydrous pearlescing base is comprised of cetyl palmitate, stearyl myristate and said solubilizing agent is present in a respective weight ratio of 1:1:15 parts by weight per 100 parts of said pearlescing base.

15. The product of the method of claim 1.
16. The product of the method of claim 2.
17. The product of the method of claim 6.
18. The product of the method of claim 12.

19. In a method for preparing an improved pearlescent shampoo containing a pearlescing agent that includes the steps of providing a liquid medium containing water, an amount of surface active agent effective for cleaning and about 0.25 to about 1.5 parts by weight per 100 parts shampoo of a water-dispersible derivative of cellulose having alkyl and hydroxyalkyl substituents on the cellulose anhydroglucose rings wherein the alkyl substituent is selected from the group consisting of methyl and ethyl and the hydroxyalkyl substituent is selected from the group consisting of 2-hydroxyethyl, 2-hydroxypropyl and 2-hydroxybutyl, which liquid medium is heated to a temperature above the melting point of the pearlescing agent and below the boiling point of the medium; admixing with stirring a pearlescing agent at a temperature above the melting point of said pearlescing agent with said heated liquid medium; maintaining the admixture so formed with stirring at a temperature above the melting point of said pearlescing agent and below the boiling point of the lowest boiling ingredient of the liquid medium for a time sufficient to form a substantially homogeneous admixture that is substantially transparent to visible light; and thereafter reducing the temperature to form a shampoo that exhibits pearlescence; the improvement which comprises:

blending and solubilizing a fatty acid ester whose fatty acid portion is derived from a $C_{16}$–$C_{22}$ fatty acid and whose alcohol portion is derived from a $C_{14}$–$C_{22}$ fatty alcohol as the pearlescing agent in a substantially anyhydrous nonionic surfactant as solubilizing agent at a weight ratio of between about 4 to about 15 parts of said solubilizing agent per part pearlescing agent to form a substantially homogeneous, liquid, anhydrous pearlescing base, said solubilizing agent being selected from the group consisting of polyoxy($C_2$–$C_4$)alkylene derivatives of $C_8$–$C_{22}$ fatty alcohols containing from about 1 to about 100 oxyethylene, oxypropylene, and oxyethylene-oxypropylene condensation units per molecule, polyoxyethylene derivatives of $C_8$–$C_{22}$ alkyl phenols containing an average of from about 3 to about 150 oxyethylene units per molecule, copolymers of ethylene oxide and propylene oxide, mono- and di-($C_2$–$C_4$)alkanolamides of $C_8$–$C_{22}$ and mixtures thereof, said blending and solubilizing being carried out prior to said admixture of said pearlescing agent and said liquid medium, and at a temperature above the melting points of both said solubilizing agent and pearlescing agent and below the boiling point of said solubilizing agent;

thereafter admixing said heated, substantially homogeneous, liquid, anhydrous pearlescing base with said heated liquid medium in an amount to provide about 0.01 to about 1.0 parts by weight of said pearlescing agent per 100 parts by weight of shampoo to form an admixture; and admixing a $C_2$–$C_4$ alkylene glycol ester of a $C_{12}$–$C_{22}$ fatty acid as a pearlescence accelerating agent to the substantially homogeneous admixture formed after admixture of said pearlescing base and said liquid medium and prior to reducing to said temperature to ambient room temperature, said pearlescence accelerating agent being admixed in a crystalline state and in an amount sufficient to provide about 0.01 to about 0.2 parts by weight per 100 parts by weight of the shampoo;

said shampoo so formed exhibiting pearlescence within a time period of about 5 days at ambient room temperature.

20. The method of claim 1 wherein said liquid medium additionally contains about 0.25 to about 1.5 parts by weight per 100 parts shampoo of a water-dispersible derivative of cellulose having alkyl and hydroxyalkyl substituents on the cellulose anhydroglucose rings wherein the alkyl substituent is selected from the group consisting of methyl and ethyl and the hydroxyalkyl substituent is selected from the group consisting of 2-hydroxyethyl, 2-hydroxypropyl and 2-hydroxybutyl.

21. The product of the method of claim 20.

22. The method of claim 20 wherein said solubilizing agent is a di-($C_2$–$C_4$)-alkanolamide of a $C_8$–$C_{22}$ fatty acid.

23. The product of the method of claim 20.

24. The product of the method of claim 22.

25. A method for preparing a substantially anhydrous pearlescing base concentrate which comprises the steps of:

(a) blending and solubilizing a pearlescing agent comprised of a fatty acid ester whose fatty acid portion is derived from a saturated $C_{16}$–$C_{22}$ fatty acid and whose alcohol portion is derived from a $C_{14}$–$C_{22}$ fatty alcohol is a substantially anhydrous nonionic surface active agent as solubilizing agent at a weight ratio of between about 1 to about 25 parts of said solubilizing agent per part pearlescing agent and at a temperature above the melting points of both said solubilizing agent and said pearlescing agent and below the boiling point of said solubilizing agent to form a substantially homogeneous, liquidm anhydrous pearlescing base concentrate, said nonionic surface active agent being selected from the group consisting of polyoxy($C_2$–$C_4$)alkylene derivatives of $C_8$–$C_{22}$ fatty alcohols containing from about 1 to about 100 oxyethylene, oxypropylene, and oxyethylene/oxypropylene condensation units per molecule, polyoxyethylene derivatives of $C_8$–$C_{22}$ alkyl phenols containing an average of from about 3 to about 150 oxyethylene units per molecule, copolymers of ethylene oxide and propylene oxide, mono- and di-($C_2$–$C_4$)alkanolamides of $C_8$–$C_{22}$ and mixtures thereof; and (b) cooling said concentrate to ambient room temperature.

26. The product of the method of claim 25.

* * * * *

UNITED STATES PATENT AND TRADEMARK OFFICE
CERTIFICATE OF CORRECTION

PATENT NO. : 4,654,207
DATED : March 31, 1987
INVENTOR(S) : John C. Preston

It is certified that error appears in the above-identified patent and that said Letters Patent is hereby corrected as shown below:

Column 25, Claim 1, line 26, "pearlscing" should read -- pearlescing --.

Claim 4, line 42, "anhvdrous" should read -- anhydrous --.

Column 28, Claim 25, line 18, "is" should read -- in --.

Claim 25, line 26, "liquidm" should read -- liquid --.

Signed and Sealed this

Second Day of August, 1988

Attest:

DONALD J. QUIGG

*Attesting Officer*  *Commissioner of Patents and Trademarks*